US012329667B2

(12) United States Patent
Burkart et al.

(10) Patent No.: US 12,329,667 B2
(45) Date of Patent: *Jun. 17, 2025

(54) STENT HAVING ADJACENT ELEMENTS CONNECTED BY FLEXIBLE WEBS

(71) Applicant: W. L. Gore & Associates, Inc., Newark, DE (US)

(72) Inventors: Dustin C. Burkart, Bellemont, AZ (US); Edward H. Cully, Clarksville, VA (US); Jeffrey B. Duncan, Flagstaff, AZ (US); Cody L. Hartman, Flagstaff, AZ (US); James D. Silverman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/529,931

(22) Filed: Dec. 5, 2023

(65) Prior Publication Data
US 2024/0173154 A1  May 30, 2024

Related U.S. Application Data

(63) Continuation of application No. 17/397,362, filed on Aug. 9, 2021, now Pat. No. 11,865,020, which is a (Continued)

(51) Int. Cl.
*A61F 2/91* (2013.01)
*A61F 2/07* (2013.01)
(Continued)

(52) U.S. Cl.
CPC ............ *A61F 2/91* (2013.01); *A61F 2/07* (2013.01); *A61F 2/86* (2013.01); *A61F 2/915* (2013.01);
(Continued)

(58) Field of Classification Search
CPC .......... A61F 2002/075; A61F 2002/826; A61F 2002/91558; A61F 2/07; A61F 2/86; A61F 2/89; A61F 2/90; A61F 2/91; A61F 2/915

See application file for complete search history.

(56) References Cited

U.S. PATENT DOCUMENTS 4,503,569 A   3/1985  Dotter
4,655,771 A   4/1987  Wallsten
(Continued)

FOREIGN PATENT DOCUMENTS

CN   101636130 A   1/2010
CN   101822868 A   9/2010
(Continued)

OTHER PUBLICATIONS

International Search Report and Written Opinion from PCT/US2009/000144, dated May 6, 2009, 14 pages.
(Continued)

*Primary Examiner* — Tuan V Nguyen

(57) ABSTRACT

A stent incorporating flexible, preferably polymeric, connecting elements into the stent wherein these elements connect adjacent, spaced-apart stent elements. Preferably the spaced-apart adjacent stent elements are the result of forming the stent from a helically wound serpentine wire having space provided between adjacent windings. Other stent forms such as multiple, individual spaced-apart ring-shaped or interconnected stent elements may also be used. The connecting elements are typically web-shaped and result from creating slits or apertures in a covering of graft material applied to the stent and then, for example, applying heat to cause the slits or apertures to enlarge. The remaining graft material forms the interconnecting webs between the adjacent stent elements.

20 Claims, 11 Drawing Sheets

Related U.S. Application Data continuation of application No. 15/915,453, filed on Mar. 8, 2018, now Pat. No. 11,103,372, which is a continuation of application No. 13/349,346, filed on Jan. 12, 2012, now Pat. No. 9,943,428, which is a continuation of application No. 12/350,921, filed on Jan. 8, 2009, now Pat. No. 8,926,688.

(60) Provisional application No. 61/020,544, filed on Jan. 11, 2008.

(51) Int. Cl.
  *A61F 2/82* (2013.01)
  *A61F 2/86* (2013.01)
  *A61F 2/90* (2013.01)
  *A61F 2/915* (2013.01)
  *A61F 2/95* (2013.01)
  *A61F 2/89* (2013.01)

(52) U.S. Cl.
  CPC ... *A61F 2002/075* (2013.01); *A61F 2002/826* (2013.01); *A61F 2002/828* (2013.01); *A61F 2/89* (2013.01); *A61F 2/90* (2013.01); *A61F 2002/91558* (2013.01)

(56) References Cited

U.S. PATENT DOCUMENTS

| | | |
|---|---|---|
| 4,739,762 A | 4/1988 | Palmaz |
| 4,776,337 A | 10/1988 | Palmaz |
| 4,884,573 A | 12/1989 | Wijay et al. |
| 5,019,090 A | 5/1991 | Pinchuk |
| 5,037,427 A | 8/1991 | Harada et al. |
| 5,061,275 A | 10/1991 | Wallsten et al. |
| 5,102,417 A | 4/1992 | Palmaz |
| 5,104,404 A | 4/1992 | Wolff |
| 5,122,154 A | 6/1992 | Rhodes |
| 5,123,917 A | 6/1992 | Lee |
| 5,201,757 A | 4/1993 | Heyn et al. |
| 5,236,447 A | 8/1993 | Kubo et al. |
| 5,282,824 A | 2/1994 | Gianturco |
| 5,300,500 A | 4/1994 | Lee et al. |
| 5,314,472 A | 5/1994 | Fontaine |
| 5,330,500 A | 7/1994 | Song |
| 5,360,443 A | 11/1994 | Barone et al. |
| 5,405,377 A | 4/1995 | Cragg |
| 5,409,495 A | 4/1995 | Osborn |
| 5,443,495 A | 8/1995 | Buscemi et al. |
| 5,443,496 A | 8/1995 | Schwartz et al. |
| 5,443,499 A | 8/1995 | Schmitt |
| 5,449,373 A | 9/1995 | Pinchasik et al. |
| 5,507,767 A | 4/1996 | Maeda et al. |
| 5,507,771 A | 4/1996 | Gianturco |
| 5,549,663 A | 8/1996 | Cottone, Jr. |
| 5,575,816 A | 11/1996 | Rudnick et al. |
| 5,591,195 A | 1/1997 | Taheri et al. |
| 5,613,979 A | 3/1997 | Trotta et al. |
| 5,662,703 A | 9/1997 | Yurek et al. |
| 5,665,115 A | 9/1997 | Cragg |
| 5,674,241 A | 10/1997 | Bley et al. |
| 5,683,448 A | 11/1997 | Cragg |
| 5,693,086 A | 12/1997 | Goicoechea et al. |
| 5,708,044 A | 1/1998 | Branca |
| 5,725,570 A | 3/1998 | Heath |
| 5,728,150 A | 3/1998 | McDonald et al. |
| 5,735,892 A | 4/1998 | Myers et al. |
| 5,749,852 A | 5/1998 | Schwab et al. |
| 5,755,774 A | 5/1998 | Pinchuk |
| 5,756,553 A | 5/1998 | Iguchi et al. |
| 5,769,884 A | 6/1998 | Solovay |
| 5,769,887 A | 6/1998 | Brown et al. |
| 5,800,456 A | 9/1998 | Maeda et al. |
| 5,800,515 A | 9/1998 | Nadal et al. |
| 5,800,521 A | 9/1998 | Orth |
| 5,814,063 A | 9/1998 | Freitag |
| 5,824,043 A | 10/1998 | Cottone, Jr. |
| 5,824,059 A | 10/1998 | Wijay |
| 5,843,092 A | 12/1998 | Heller et al. |
| 5,843,161 A | 12/1998 | Solovay |
| 5,873,906 A | 2/1999 | Lau et al. |
| 5,876,432 A | 3/1999 | Lau et al. |
| 5,879,369 A | 3/1999 | Ishida |
| 5,891,193 A | 4/1999 | Robinson et al. |
| 5,899,934 A | 5/1999 | Amundson et al. |
| 5,906,639 A | 5/1999 | Rudnick et al. |
| 5,919,225 A | 7/1999 | Lau et al. |
| 5,922,020 A | 7/1999 | Klein et al. |
| 5,968,091 A | 10/1999 | Pinchuk et al. |
| 5,984,957 A | 11/1999 | Laptewicz et al. |
| 6,001,125 A | 12/1999 | Golds et al. |
| 6,004,348 A | 12/1999 | Banas et al. |
| 6,007,545 A | 12/1999 | Venturelli |
| 6,013,854 A | 1/2000 | Moriuchi |
| 6,015,432 A | 1/2000 | Rakos et al. |
| 6,016,846 A | 1/2000 | Knittel et al. |
| 6,022,359 A | 2/2000 | Frantzen |
| 6,022,374 A | 2/2000 | Imran |
| 6,048,360 A | 4/2000 | Khosravi et al. |
| 6,071,307 A | 6/2000 | Rhee et al. |
| 6,077,296 A | 6/2000 | Shokoohi et al. |
| 6,107,004 A | 8/2000 | Donadio, III |
| 6,123,712 A | 9/2000 | Di et al. |
| 6,139,573 A | 10/2000 | Sogard et al. |
| 6,139,575 A | 10/2000 | Shu et al. |
| 6,143,022 A | 11/2000 | Shull et al. |
| 6,146,417 A | 11/2000 | Ischinger |
| 6,159,219 A | 12/2000 | Ren |
| 6,159,239 A | 12/2000 | Greenhalgh |
| 6,165,210 A | 12/2000 | Lau et al. |
| 6,171,334 B1 | 1/2001 | Cox |
| 6,174,328 B1 | 1/2001 | Cragg |
| 6,217,609 B1 | 4/2001 | Haverkost |
| 6,231,597 B1 | 5/2001 | Deem et al. |
| 6,264,687 B1 | 7/2001 | Tomonto |
| 6,283,990 B1 | 9/2001 | Kanesaka |
| 6,283,992 B1 | 9/2001 | Hankh et al. |
| 6,287,333 B1 | 9/2001 | Appling et al. |
| 6,290,722 B1 | 9/2001 | Wang |
| 6,312,458 B1 | 11/2001 | Golds |
| 6,315,791 B1 | 11/2001 | Gingras et al. |
| 6,315,792 B1 | 11/2001 | Armstrong et al. |
| 6,331,188 B1 | 12/2001 | Lau et al. |
| 6,331,190 B1 | 12/2001 | Shokoohi et al. |
| 6,334,868 B1 | 1/2002 | Ham |
| 6,336,937 B1 | 1/2002 | Vonesh et al. |
| 6,340,366 B2 | 1/2002 | Wijay |
| 6,344,054 B1 | 2/2002 | Parodi |
| 6,350,277 B1 | 2/2002 | Kocur |
| 6,355,055 B1 | 3/2002 | Waksman et al. |
| 6,357,104 B1 | 3/2002 | Myers |
| 6,361,637 B2 | 3/2002 | Martin et al. |
| 6,364,903 B2 | 4/2002 | Tseng et al. |
| 6,387,122 B1 | 5/2002 | Cragg |
| 6,398,803 B1 | 6/2002 | Layne et al. |
| 6,409,754 B1 | 6/2002 | Smith et al. |
| 6,419,685 B2 | 7/2002 | Di et al. |
| 6,432,133 B1 | 8/2002 | Lau et al. |
| 6,436,132 B1 | 8/2002 | Patel et al. |
| 6,451,050 B1 | 9/2002 | Rudakov et al. |
| 6,461,380 B1 | 10/2002 | Cox |
| 6,464,718 B1 | 10/2002 | Miller et al. |
| 6,488,701 B1 | 12/2002 | Nolting et al. |
| 6,488,705 B2 | 12/2002 | Schmitt et al. |
| 6,497,722 B1 | 12/2002 | Von et al. |
| 6,500,203 B1 | 12/2002 | Thompson et al. |
| 6,503,556 B2 | 1/2003 | Harish et al. |
| 6,506,202 B1 | 1/2003 | Dutta et al. |
| 6,511,496 B1 | 1/2003 | Huter et al. |
| 6,520,986 B2 | 2/2003 | Martin et al. |
| 6,527,739 B1 | 3/2003 | Bigus et al. |
| 6,537,311 B1 | 3/2003 | Cox et al. |
| 6,540,773 B2 | 4/2003 | Dong |
| 6,540,776 B2 | 4/2003 | Sanders et al. |

(56) References Cited

U.S. PATENT DOCUMENTS

| | | |
|---|---|---|
| 6,541,589 B1 | 4/2003 | Baillie |
| 6,551,350 B1 | 4/2003 | Thornton et al. |
| 6,551,352 B2 | 4/2003 | Clerc et al. |
| 6,554,848 B2 | 4/2003 | Boylan et al. |
| 6,558,414 B2 | 5/2003 | Layne |
| 6,558,415 B2 | 5/2003 | Thompson |
| 6,565,599 B1 | 5/2003 | Hong et al. |
| 6,579,305 B1 | 6/2003 | Lashinski |
| 6,585,755 B2 | 7/2003 | Jackson et al. |
| 6,589,275 B1 | 7/2003 | Ivancev et al. |
| 6,589,276 B2 | 7/2003 | Pinchasik et al. |
| 6,602,284 B2 | 8/2003 | Cox et al. |
| 6,605,056 B2 | 8/2003 | Eidenschink et al. |
| 6,607,551 B1 | 8/2003 | Sullivan et al. |
| 6,616,689 B1 | 9/2003 | Ainsworth et al. |
| 6,620,128 B1 | 9/2003 | Simhambhatla |
| 6,620,193 B1 | 9/2003 | Lau et al. |
| 6,626,939 B1 | 9/2003 | Burnside et al. |
| 6,629,992 B2 | 10/2003 | Bigus et al. |
| 6,645,239 B1 | 11/2003 | Park et al. |
| 6,652,574 B1 | 11/2003 | Jayaraman |
| 6,652,579 B1 | 11/2003 | Cox et al. |
| 6,669,719 B2 | 12/2003 | Wallace et al. |
| 6,673,103 B1 | 1/2004 | Golds et al. |
| 6,689,162 B1 | 2/2004 | Thompson |
| 6,709,454 B1 | 3/2004 | Cox et al. |
| 6,712,357 B1 | 3/2004 | Tranquilla |
| 6,713,357 B1 | 3/2004 | Wang et al. |
| 6,730,117 B1 | 5/2004 | Tseng et al. |
| 6,740,114 B2 | 5/2004 | Burgermeister |
| 6,749,584 B2 | 6/2004 | Briggs et al. |
| 6,770,087 B2 | 8/2004 | Layne et al. |
| 6,770,089 B1 | 8/2004 | Hong et al. |
| 6,776,771 B2 | 8/2004 | Van et al. |
| 6,805,705 B2 | 10/2004 | Hong et al. |
| 6,849,086 B2 | 2/2005 | Cragg |
| 6,866,805 B2 | 3/2005 | Hong et al. |
| 6,872,433 B2 | 3/2005 | Seward et al. |
| 6,881,216 B2 | 4/2005 | Di et al. |
| 6,881,221 B2 | 4/2005 | Golds |
| 6,887,266 B2 | 5/2005 | Williams et al. |
| 6,893,457 B2 | 5/2005 | Dong |
| 6,923,827 B2 | 8/2005 | Campbell et al. |
| 6,945,991 B1 | 9/2005 | Brodeur et al. |
| 6,960,186 B1 | 11/2005 | Fukaya et al. |
| 7,105,018 B1 | 9/2006 | Yip et al. |
| 7,105,021 B2 | 9/2006 | Edens et al. |
| 7,108,716 B2 | 9/2006 | Burnside et al. |
| 7,112,293 B2 | 9/2006 | Dubson et al. |
| 7,115,220 B2 | 10/2006 | Dubson et al. |
| 7,118,592 B1 | 10/2006 | Dang et al. |
| 7,141,062 B1 | 11/2006 | Pinchasik et al. |
| 7,144,422 B1 | 12/2006 | Rao |
| 7,163,533 B2 | 1/2007 | Hobbs et al. |
| 7,163,553 B2 | 1/2007 | Limon |
| 7,186,263 B2 | 3/2007 | Golds et al. |
| 7,258,697 B1 | 8/2007 | Cox et al. |
| 7,273,495 B2 | 9/2007 | Limon |
| 7,288,111 B1 | 10/2007 | Holloway et al. |
| 7,314,480 B2 | 1/2008 | Eidenschink et al. |
| 7,323,008 B2 | 1/2008 | Kantor et al. |
| 7,329,276 B2 | 2/2008 | Smith et al. |
| 7,384,411 B1 | 6/2008 | Condado |
| 7,455,687 B2 | 11/2008 | Saunders et al. |
| 7,510,571 B2 | 3/2009 | Spiridigliozzi et al. |
| 7,540,879 B2 | 6/2009 | Lualdi |
| 7,578,831 B2 | 8/2009 | Von et al. |
| 7,686,841 B2 | 3/2010 | Eidenschink et al. |
| 7,691,461 B1 | 4/2010 | Prabhu |
| 7,704,274 B2 | 4/2010 | Boyle et al. |
| 7,727,271 B2 | 6/2010 | Kujawski et al. |
| 7,967,836 B2 | 6/2011 | Warnack et al. |
| 8,066,667 B2 | 11/2011 | Hayman et al. |
| 8,221,484 B2 | 7/2012 | Wesselmann |
| 8,257,432 B2 | 9/2012 | Kaplan et al. |
| 8,444,686 B2 | 5/2013 | Holman et al. |
| 8,585,640 B2 | 11/2013 | Alpini et al. |
| 8,597,566 B2 | 12/2013 | Eskaros et al. |
| 8,672,990 B2 | 3/2014 | Holman et al. |
| 8,858,863 B2 | 10/2014 | Venturelli |
| 8,926,688 B2 | 1/2015 | Burkart et al. |
| 8,979,886 B2 | 3/2015 | Campbell et al. |
| 9,149,612 B2 | 10/2015 | Chuter |
| 9,370,643 B2 | 6/2016 | Hedberg et al. |
| 9,370,647 B2 | 6/2016 | Campbell et al. |
| 9,622,888 B2 | 4/2017 | Armstrong et al. |
| 9,669,194 B2 | 6/2017 | Campbell et al. |
| 9,682,219 B2 | 6/2017 | Venturelli |
| 9,770,352 B2 | 9/2017 | Kanjickal et al. |
| 9,901,715 B2 | 2/2018 | Cully et al. |
| 9,943,428 B2 | 4/2018 | Burkart et al. |
| 10,299,948 B2 | 5/2019 | Bohn et al. |
| 10,456,281 B2 | 10/2019 | Armstrong et al. |
| 10,463,519 B2 | 11/2019 | Aggerholm et al. |
| 10,470,905 B2 | 11/2019 | Yang et al. |
| 10,543,116 B2 | 1/2020 | Bohn et al. |
| 10,568,752 B2 | 2/2020 | Kovach et al. |
| 11,779,481 B2 | 10/2023 | Kovach et al. |
| 2001/0020181 A1 | 9/2001 | Layne |
| 2001/0025130 A1 | 9/2001 | Tomonto |
| 2001/0027329 A1 | 10/2001 | Simhambhatla et al. |
| 2001/0032009 A1 | 10/2001 | Layne et al. |
| 2002/0007102 A1 | 1/2002 | Salmon et al. |
| 2002/0013617 A1 | 1/2002 | Matsutani et al. |
| 2002/0049408 A1 | 4/2002 | Van et al. |
| 2002/0077690 A1 | 6/2002 | Wang |
| 2002/0099431 A1 | 7/2002 | Armstrong et al. |
| 2002/0111668 A1 | 8/2002 | Smith |
| 2002/0151964 A1 | 10/2002 | Smith et al. |
| 2002/0165601 A1 | 11/2002 | Clerc |
| 2003/0060756 A1 | 3/2003 | Hayman et al. |
| 2003/0114909 A1 | 6/2003 | Clerc et al. |
| 2003/0208260 A1 | 11/2003 | Lau et al. |
| 2003/0236563 A1 | 12/2003 | Fifer |
| 2004/0019373 A1 | 1/2004 | Casey et al. |
| 2004/0024442 A1 | 2/2004 | Sowinski et al. |
| 2004/0024448 A1 | 2/2004 | Chang et al. |
| 2004/0030377 A1 | 2/2004 | Dubson et al. |
| 2004/0033364 A1 | 2/2004 | Spiridigliozzi et al. |
| 2004/0096532 A1 | 5/2004 | Dubson et al. |
| 2004/0096533 A1 | 5/2004 | Dubson et al. |
| 2004/0106980 A1 | 6/2004 | Solovay et al. |
| 2004/0138731 A1 | 7/2004 | Johnson |
| 2004/0143272 A1 | 7/2004 | Cully et al. |
| 2004/0167635 A1 | 8/2004 | Yachia et al. |
| 2004/0172127 A1 | 9/2004 | Kantor |
| 2004/0236402 A1 | 11/2004 | Layne et al. |
| 2005/0004647 A1 | 1/2005 | Bassoe |
| 2005/0010281 A1 | 1/2005 | Yodfat et al. |
| 2005/0125071 A1 | 6/2005 | Nahleili |
| 2005/0137675 A1 | 6/2005 | Dubson et al. |
| 2005/0154449 A1 | 7/2005 | Elmaleh |
| 2005/0182474 A1 | 8/2005 | Jones et al. |
| 2005/0186243 A1 | 8/2005 | Hunter et al. |
| 2005/0209672 A1 | 9/2005 | George et al. |
| 2005/0228480 A1 | 10/2005 | Douglas et al. |
| 2006/0009835 A1 | 1/2006 | Osborne et al. |
| 2006/0036308 A1 | 2/2006 | Goshgarian |
| 2006/0036311 A1 | 2/2006 | Nakayama et al. |
| 2006/0085065 A1 | 4/2006 | Krause et al. |
| 2006/0122691 A1 | 6/2006 | Richter |
| 2006/0184237 A1 | 8/2006 | Weber et al. |
| 2006/0190072 A1 | 8/2006 | Das |
| 2006/0259133 A1 | 11/2006 | Sowinski et al. |
| 2006/0266474 A1 | 11/2006 | Burnside et al. |
| 2006/0271091 A1 | 11/2006 | Campbell et al. |
| 2006/0271157 A1 | 11/2006 | Edens et al. |
| 2006/0271165 A1 | 11/2006 | Yip et al. |
| 2006/0287709 A1 | 12/2006 | Rao |
| 2006/0293743 A1 | 12/2006 | Andersen et al. |
| 2007/0055365 A1 | 3/2007 | Greenberg et al. |
| 2007/0073383 A1 | 3/2007 | Yip et al. |
| 2007/0129791 A1 | 6/2007 | Balaji |
| 2007/0208412 A1 | 9/2007 | Elmaleh |

(56) References Cited

U.S. PATENT DOCUMENTS

| | | |
|---|---|---|
| 2007/0213804 A1 | 9/2007 | Kaplan et al. |
| 2007/0239264 A1 | 10/2007 | Fliedner |
| 2007/0250146 A1 | 10/2007 | Cully et al. |
| 2008/0161901 A1 | 7/2008 | Heuser et al. |
| 2008/0319388 A1 | 12/2008 | Slattery et al. |
| 2009/0018635 A1 | 1/2009 | Holman et al. |
| 2009/0054967 A1 | 2/2009 | Das |
| 2009/0069878 A1 | 3/2009 | Weber et al. |
| 2009/0112306 A1* | 4/2009 | Bonsignore ............. A61F 2/915 623/1.49 |
| 2009/0138070 A1 | 5/2009 | Holzer et al. |
| 2009/0182413 A1 | 7/2009 | Burkart et al. |
| 2009/0234429 A1 | 9/2009 | Lau |
| 2009/0283206 A1 | 11/2009 | Eskaros et al. |
| 2010/0069839 A1 | 3/2010 | Holman et al. |
| 2010/0222870 A1 | 9/2010 | Kaplan et al. |
| 2010/0228333 A1 | 9/2010 | Drasler et al. |
| 2011/0046717 A1 | 2/2011 | Issenmann et al. |
| 2011/0087191 A1 | 4/2011 | Scheuermann |
| 2011/0264192 A1 | 10/2011 | Hartley et al. |
| 2012/0071912 A1 | 3/2012 | Campbell et al. |
| 2012/0109283 A1 | 5/2012 | Burkart et al. |
| 2012/0253380 A1 | 10/2012 | Venturelli |
| 2012/0330232 A1 | 12/2012 | Hedberg et al. |
| 2013/0018406 A1 | 1/2013 | Campbell et al. |
| 2013/0184807 A1 | 7/2013 | Kovach et al. |
| 2013/0253466 A1 | 9/2013 | Campbell et al. |
| 2013/0261731 A1 | 10/2013 | Zhou et al. |
| 2014/0066896 A1 | 3/2014 | Tilson et al. |
| 2014/0066897 A1 | 3/2014 | Campbell et al. |
| 2014/0066898 A1 | 3/2014 | Cully et al. |
| 2014/0135891 A1 | 5/2014 | Poehlmann et al. |
| 2014/0142684 A1 | 5/2014 | Zukowski |
| 2014/0172066 A1 | 6/2014 | Goepfrich et al. |
| 2014/0276406 A1 | 9/2014 | Campbell et al. |
| 2014/0277331 A1 | 9/2014 | Ngo et al. |
| 2014/0277346 A1 | 9/2014 | Kanjickal et al. |
| 2014/0277374 A1 | 9/2014 | Kovach |
| 2014/0378896 A1 | 12/2014 | Venturelli |
| 2015/0133988 A1 | 5/2015 | Chuter |
| 2016/0143759 A1 | 5/2016 | Bohn et al. |
| 2016/0243340 A1 | 8/2016 | Campbell et al. |
| 2017/0172776 A1 | 6/2017 | Kanjickal et al. |
| 2017/0340464 A1 | 11/2017 | Kovach et al. |
| 2017/0340465 A1 | 11/2017 | Kanjickal et al. |
| 2017/0348124 A1 | 12/2017 | Wang |
| 2018/0049898 A1 | 2/2018 | Armstrong et al. |
| 2018/0193177 A1 | 7/2018 | Burkart et al. |
| 2018/0296377 A1 | 10/2018 | Bohn et al. |
| 2019/0209739 A1 | 7/2019 | Goepfrich et al. |
| 2019/0298556 A1 | 10/2019 | Bohn et al. |
| 2019/0388252 A1 | 12/2019 | Armstrong et al. |
| 2020/0253763 A1 | 8/2020 | Kovach et al. |
| 2021/0236314 A1 | 8/2021 | Bohn et al. |
| 2021/0361451 A1 | 11/2021 | Burkart et al. |
| 2022/0168124 A1 | 6/2022 | Bohn et al. |
| 2024/0074884 A1 | 3/2024 | Kovach et al. |
| 2024/0082031 A1 | 3/2024 | Bohn et al. |

FOREIGN PATENT DOCUMENTS

| | | |
|---|---|---|
| CN | 101909545 A | 12/2010 |
| CN | 102940543 A | 2/2013 |
| CN | 103260549 A | 8/2013 |
| CN | 103561686 A | 2/2014 |
| CN | 103702709 A | 4/2014 |
| CN | 103930157 A | 7/2014 |
| CN | 103930158 A | 7/2014 |
| CN | 105050550 A | 11/2015 |
| EP | 0745395 A2 | 12/1996 |
| EP | 0951877 A2 | 10/1999 |
| EP | 1110561 A2 | 6/2001 |
| EP | 1550477 A1 | 7/2005 |
| EP | 1927327 A2 | 6/2008 |
| JP | 09-099087 A | 4/1997 |
| JP | 11-299901 A | 11/1999 |
| JP | 2002-501404 A | 1/2002 |
| JP | 2005-535414 A | 11/2005 |
| JP | 2010-500107 A | 1/2010 |
| JP | 2011-206124 A | 10/2011 |
| JP | 2014-520632 A | 8/2014 |
| JP | 2014-530045 A | 11/2014 |
| JP | 2015-534883 A | 12/2015 |
| JP | 2016-506271 A | 3/2016 |
| WO | 95/17223 A1 | 6/1995 |
| WO | 95/26695 A2 | 10/1995 |
| WO | 96/21404 A1 | 7/1996 |
| WO | 96/38109 A1 | 12/1996 |
| WO | 98/31305 A1 | 7/1998 |
| WO | 99/17680 A1 | 4/1999 |
| WO | 99/34855 A1 | 7/1999 |
| WO | 00/42949 A2 | 7/2000 |
| WO | 00/43051 A1 | 7/2000 |
| WO | 00/45741 A1 | 8/2000 |
| WO | 00/49971 A1 | 8/2000 |
| WO | 01/21101 A1 | 3/2001 |
| WO | 02/22024 A2 | 3/2002 |
| WO | 03/13337 A2 | 2/2003 |
| WO | 03/07795 A3 | 4/2003 |
| WO | 03/57075 A2 | 7/2003 |
| WO | 03/57077 A1 | 7/2003 |
| WO | 2004/016199 A1 | 2/2004 |
| WO | 2004/093941 A2 | 11/2004 |
| WO | 2005/096997 A2 | 10/2005 |
| WO | 2006/029617 A1 | 3/2006 |
| WO | 2006/081568 A1 | 8/2006 |
| WO | 2006/124824 A1 | 11/2006 |
| WO | 2008/019022 A1 | 2/2008 |
| WO | 2009/009635 A1 | 1/2009 |
| WO | 2009/066330 A1 | 5/2009 |
| WO | 2010/037141 A1 | 4/2010 |
| WO | 2013/009740 A1 | 1/2013 |
| WO | 2013/040522 A2 | 3/2013 |
| WO | 2013/096854 A3 | 8/2013 |
| WO | 2013/162685 A1 | 10/2013 |
| WO | 2014/078558 A1 | 5/2014 |
| WO | 2014/152684 A2 | 9/2014 |
| WO | 2014/158516 A1 | 10/2014 |
| WO | 2015/073114 A1 | 5/2015 |
| WO | 2016/086202 A2 | 6/2016 |
| WO | 2017/204838 A1 | 11/2017 |
| WO | 2018/039444 A1 | 3/2018 |

OTHER PUBLICATIONS

International Search Report and Written Opinion issued in PCT/US2009/000144, mailed Jun. 5, 2009, 14 pages.

Nakayama Y, Nishi S, Ueda H, et al. Fabrication of micropored elastomeric film covered stents and acute-phase performances. Development of Covered Stents 2002; 52-61.

Nishi, S. et al., "Newly Developed Stent Graft with Micropored and Heparin Impregnated SPU Film, Long-Term Follow-up Study in Vivo", Interventional Neuroradiology, 7 (Suppl 1): 161-166, 2001.

Wilson, Eric et al., "Deployment and Healing of an ePTFE Encapsulated Stent Endograft in the Canine Aorta," Annals of Vascular Surgery, (1997), vol. 11, No. 4, pp. 354-358.

* cited by examiner

STENT HAVING ADJACENT ELEMENTS CONNECTED BY FLEXIBLE WEBS

CROSS REFERENCE TO RELATED APPLICATIONS

This application is a continuation of U.S. application Ser. No. 17/397,362, filed Aug. 9, 2021, which is a continuation of U.S. application Ser. No. 15/915,453, filed Mar. 8, 2018, now U.S. Pat. No. 11,103,372, issued Aug. 31, 2021, which is a continuation of U.S. application Ser. No. 13/349,346, filed Jan. 12, 2012, now U.S. Pat. No. 9,943,428, issued Apr. 17, 2018, which is a continuation of U.S. application Ser. No. 12/350,921, filed Jan. 8, 2009, now U.S. Pat. No. 8,926,688, issued Jan. 6, 2015, which claims the benefit of U.S. Provisional Patent Application No. 61/020,544, filed on Jan. 11, 2008, all of which are incorporated herein by reference in their entireties for all purposes.

FIELD OF THE INVENTION

The present invention relates to the field of implantable stents having flexibly connected adjacent stent elements.

BACKGROUND OF THE INVENTION

The use of implantable stents in the vasculature and other body conduits has become commonplace since first proposed by Dotter in the 1960's. These devices are required to have a small, compacted diameter for insertion into an intended body conduit and transport, typically via a catheter, to a desired site for deployment, at which site they are expanded to a larger diameter as necessary to fit interferably with the luminal surface of the body conduit. Balloon expandable stents are expanded by plastically deforming the device with an inflatable balloon on which the expandable stent was previously mounted in the compacted state, the balloon being attached to the distal end of the catheter and inflated via the catheter. Self-expanding stents are forcibly compacted to a small diameter and restrained at that diameter by a constraining sleeve or other means. Following delivery to a desired site for deployment, they are released from the restraint and spring open to contact the luminal surface of the body conduit. These devices are typically made from nitinol metal alloys and typically rely on the superelastic and biocompatible character of this metal. Nitinol stents that rely on the shape memory attributes of that material are also known.

The evolution of implantable stents has also included the use of a tubular covering fitted to the stent, either to the outer surface, the luminal surface or to both surfaces of the stent. These covered stents have generally come to be referred to as stent-grafts. The coverings are generally of a polymeric biocompatible material such as polyethylene terephthalate (PET) or polytetrafluoroethylene (PTFE). See, for example, U.S. Pat. No. 4,776,337 to Palmaz.

The Palmaz '337 patent also describes that the covering may be optionally provided with perforations if desired for particular applications. Because of the open area provided by the perforations, such devices having perforated coverings may be considered to be a sort of hybrid stent and stent-graft, as are devices that include stent frames having metallic stent elements and polymeric elements connecting, covering or other otherwise being attached to the stent elements. The presence of the polymeric elements reduces the otherwise open space between the adjacent metallic stent elements, either very slightly or very substantially depending on the intended application and mechanical design. Perforated stent-grafts are also described elsewhere; see, for example WO00/42949.

Stents having stent elements provided with polymeric coatings or coverings are also known; see, for example, U.S. Pat. No. 5,735,892 to Myers et al. and U.S. Pat. No. 5,968,091 to Pinchuk et al.

Generally, a fully covered stent-graft can be considered to have a surface area (hereinafter $A_{max}$) equal to the outer circumference of the expanded stent multiplied by the length of the stent. For a conventional, open frame stent (as opposed to a stent-graft), the surface area represented by all of the stent elements is only a small portion of the maximum surface area $A_{max}$. The actual surface area covered by the stent, meaning the area covered by all components of the stent (including connecting elements) in their deployed state, is $A_{stent}$. The porosity index, or P.I., describes the open area (the portion of the maximum surface area not covered by all components of the stent assembly) as a percentage of maximum surface area, wherein:

$$P.I.=(1-(A_{stent}/A_{max}))\times 100\%.$$

A preferred method of measuring the actual surface area covered by the stent ($A_{stent}$), involves the use of a machine provided Visicon Inspection Technologies, LLC (Napa, CA). The Visicon Finescan™ Stent Inspection System (Visicon Finescan machine model 85) uses a 6000 pixel line scan camera to generate a flat, unrolled view of a stent. In operation, the stent is mounted on a sapphire mandrel with a fine diffuse surface. This mandrel is held under the linear array camera and rotated by the system electronics and is used to trigger the linear array camera to collect a line of image data in a precise line-by-line manner. After a complete revolution an entire image of the stent is acquired. When the entire stent has been imaged, the software differentiates between the stent with cover and the background. The total number of picture elements (pixels) is compared to the total number of pixels associated with the stent and cover to determine $A_{stent}$. Basic settings on the machine used for this type of determination are (for example): light, 100%; exposure, 0.3 ms/line; gain, 5; threshold, 50; noise filter, 20; smoothing, 4.

The open area may be a continuous single space, such as the space between windings of a single helically wound stent element. Likewise the open area may be represented by the space between multiple individual annular or ring-shaped stent elements. The open area may also be represented by the total area of multiple apertures provided by either a single stent element (e.g., as shown by FIGS. 1B and 2B of U.S. Pat. No. 4,776,337 to Palmaz) or by multiple stent elements providing multiple apertures. If multiple apertures are provided they may be of equal or unequal sizes. The use of a perforated graft covering or of polymeric elements in addition to metallic stent elements may also reduce the open area.

Stents having a porosity index of greater than 50% are considered to be substantially open stents.

In addition to the porosity index, the size of any aperture providing the open area must be considered if it is intended to cover only a portion of a stent area for a specific stent application. For multiple apertures, often the consideration must be for the largest size of any individual aperture, particularly if the apertures are to provide for a "filtering" effect whereby they control or limit the passage of biologic materials from the luminal wall into the flow space of the body conduit.

Various stent devices combining metallic stent elements with polymeric connecting elements are known; see, for example U.S. Pat. No. 5,507,767 to Maeda et al. Another is a stent provided with a flexible knitted sleeve having small open apertures in the fashion of chain link fencing, from InspireMD Ltd. (4 Derech Hashalom St., Tel Aviv 67892 Israel).

SUMMARY OF THE INVENTION

An open stent (a stent having open space through its thickness at locations between the ends of the stent) and method of making are described. The stent incorporates flexible, preferably polymeric connecting elements (i.e., polymeric webs) into the stent wherein these connecting elements connect adjacent, spaced-apart stent elements. The flexible, preferably polymeric connecting elements provide a means for keeping the stent elements equally spaced and allow the construction of a stent having good flexibility and a useful resistance to forces that may be applied to the device in vivo such as torsional forces, bending forces, axial tension or compression, or radial compression.

Preferably the spaced-apart adjacent stent elements are in the form of a helically wound serpentine wire having space provided between adjacent windings. Other stent forms such as multiple, individual spaced-apart ring-shaped stent elements may also be used. Ring shaped stent elements may be in the form of zig-zag elements creating a circumferential ring, or interconnected elements that provide diamond shaped openings in a circumferential sequence when the device is diametrically expanded. Alternatively, embodiments presented that utilize the helically wound serpentine forms are preferred for many applications. The stent is preferably self-expanding (made from materials such as nitinol) but may also be made from materials suitable for balloon expandable stents (e.g., stainless steel, magnesium based alloys, magnesium, cobalt chromium alloy, titanium or titanium based alloys).

Helically wound stent frames are inherently unstable in absence of a secondary linkage connecting adjacent rows. Utilization of the described polymer web linkage to interconnect adjacent rows stabilizes the helical structure and limits axial elongation, torsion and bending while allowing a high degree of flexibility.

The adjacent, spaced-apart stent elements are preferably substantially circumferentially oriented, meaning that they have a general direction of orientation perpendicular to the longitudinal axis of the stent, when the stent is in a straight, unbent state.

A method of making involves the application of a biocompatible polymeric covering to the chosen stent form to create, temporarily, a stent-graft. The covering is preferably of a strong and thin material and may be in a tubular form, although sheet forms (e.g., relatively wide films cut into narrow tapes) are preferred for manufacturing as will be described. The covering is preferably applied to the outer surface of the stent, but may be applied only to the luminal surface, or alternatively may be applied to both the luminal and abluminal (outer) surfaces of the stent. Covering both the luminal and abluminal surfaces allows for the possibility of covering substantially all of the metallic surfaces of the stent with the desired polymer. The polymeric film covering is preferably a thermoplastic film, and preferably a film with strength properties that result in relatively uniform directional shrinking properties when the film is subjected to heat above its melt point. The film-covered stent graft is provided with punctures (slits or other apertures) through the thickness of the film, preferably at locations between adjacent stent elements as will be further described. The punctured stent-graft is then exposed to heat above the melt temperature of the film which causes the film to shrink back from the edges of the previously created puncture, resulting in openings through the wall of the stent. These openings are of size, shape, quantity and orientation that are a result of the size, shape, quantity and orientation of the previously created punctures, the amount of heat subsequently applied and the thickness and type of polymeric film used.

It is apparent that these are manufacturing variables that may be controlled as desired. The resulting open area of the stent (i.e., porosity index) may cover a wide range (i.e., 10%, 20%, 30%, 40%, 50%, 60%, 70%, 75%, 80%, 85%, 90%, 95%, or higher, or between any of these percentages). The remaining polymeric film following the heating step is in the form of polymeric webs extending between the adjacent stent elements.

An alternate method of making also involves the application of a biocompatible polymeric covering to the chosen stent form to create, temporarily, a stent-graft. A preferable stent form in this instance would be ring shaped stent elements made from a suitable balloon expandable material. The covering is similar to that described previously and may be applied to the chosen stent form similarly to the methods described in the previous section. The polymeric film covering is preferably a thermoplastic film, and preferably a film with unidirectional strength properties. The film-covered stent graft is provided with punctures (slits or other apertures) through the thickness of the film, preferably at locations between adjacent stent elements as will be further described. The punctured stent graft is then exposed to heat sufficient to bond the film to the stent form. When the resulting stent is diametrically expanded, these openings are of size, shape, quantity and orientation that are a result of the size, shape, quantity, and orientation of the previously created punctures. It is apparent that these are manufacturing variables that may be controlled as desired. The resulting open area of the stent (i.e., porosity index) may cover a wide range such as previously described. The remaining polymeric film following the puncturing/slitting step is in the form of polymeric webs extending between and interconnecting the adjacent stent elements.

Further, the finished open frame stent may optionally be provided with another covering of polymeric graft material to create a stent-graft if desired. This graft covering is easily adhered or bonded to the covering or coating that is provided over the stent elements (e.g., the wire) and forms the interconnecting webs.

The polymeric covering of these finished devices (that include a multiplicity of openings and a multiplicity of polymeric interconnecting webs) is generally continuous or substantially continuous between the stent ends, being the result of having been made from a continuous sheet of film or the result using helically wrapped polymeric tape with overlapping adjacent edges that are melt-bonded together. The film covering that forms these continuous webs is well adhered to the stent elements.

Still further, these devices may be provided with coatings (preferably elutable coatings) of various therapeutic agents (e.g., heparin) by various means known in the art that are suitable to the particular agent.

Stents made as described herein have good conformability enabled by the flexible interconnecting webs between adjacent stent elements that provide flexibility and anatomic apposition. They also have good flexural durability enabled by interconnecting webs between adjacent stent elements that mitigates fracture due to cyclic longitudinal bending in curved anatomies. The expandable device is scalable to accommodate a range of vessel sizes (e.g. 3 mm-55 mm).

The potential clinical applications of the expandable device described herein include but are not limited to: congenital defects (i.e., pulmonary artery stenosis, aortic coarctation), adjunctive aortic therapy (i.e., Type I endoleaks; aortic side branch stenting), peripheral artery disease (i.e., renal and iliac artery stenosis, aneurysm, and dissection) and venous applications.

DETAILED DESCRIPTION OF THE DRAWINGS

Figure 1A:
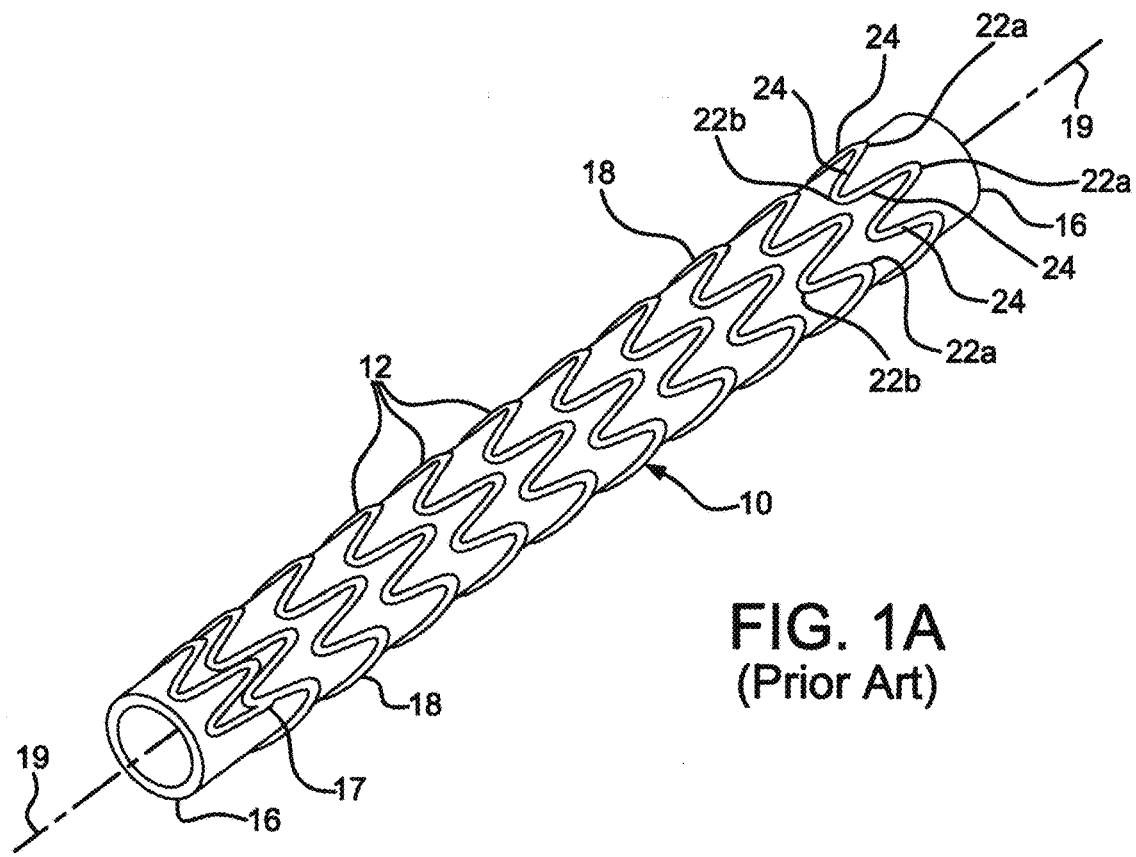
FIGS. 1A and 1B describe respectively a perspective view and a plan view of a helically wound serpentine wire form (previously known) of a preferred stent as described herein.

It has been noted that a variety of stent forms may be usefully provided with the flexible connecting elements taught herein. FIG. 1A shows a perspective view of a stent 10 that is preferred for use as described herein. The stent 10 shown comprises a helical winding of a length of serpentine wire 18. Sequential windings of the helical wound serpentine wire 18 result in spaced-apart adjacent stent elements 12. The ends 17 of wire 18 may be secured by any suitable method (e.g., welding) to the adjacent helical winding. For clarity, stent 10 is shown with a mandrel 16 extending through and beyond both ends of the stent lumen, making the side closest to the viewer visually apparent while blocking the view of the side of stent 10 furthest from the viewer. Mandrel 16 is present only for clarity of visualization and is not a part of stent 10.

The helically wound serpentine wire 18 extends continuously between opposing ends of stent 10, wherein opposing apices 22a and 22b formed of wire bends of relatively small radii are interconnected by straight or relatively straight wire segments 24. The apices typically "point" in directions that are substantially parallel to the longitudinal axis 19 of the mandrel 16 and the tubular form of the stent 10, with alternating apices 22a and 22b pointing in opposite directions, that is, pointing to opposite ends of the stent. As shown by FIG. 1A, it is preferred that apices pointing in one direction (e.g., apices 22a) are aligned along a first common line while the apices pointing in the opposite direction (e.g., apices 22b) are aligned along a second common line that is parallel to the first common line.

Figure 1B:
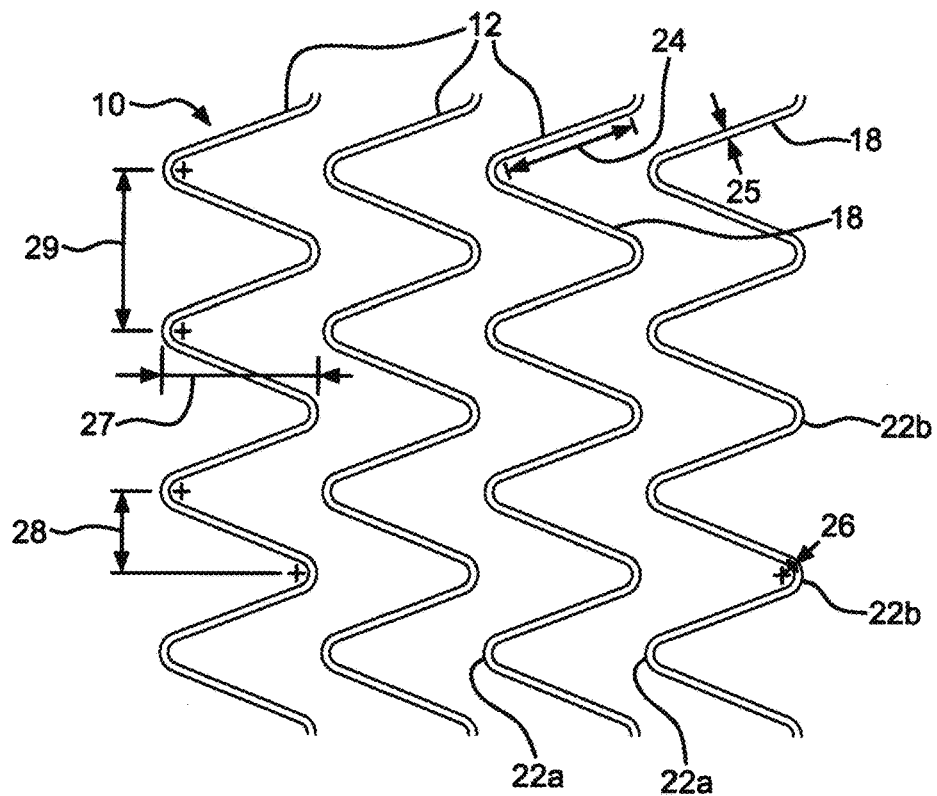

FIG. 1B shows a plan (or flattened) view of details of the serpentine wire form described by FIG. 1A; dimensions relate to the method of making described below. Dimension 27 is considered as the height (amplitude) of adjacent opposing apices while dimension 28 is the width of adjacent opposing apices. Dimension 29 describes one full period of the serpentine form. Wire diameter 25 and bend radius 26 of the apices 22 may be chosen as appropriate.

Figure 2A:
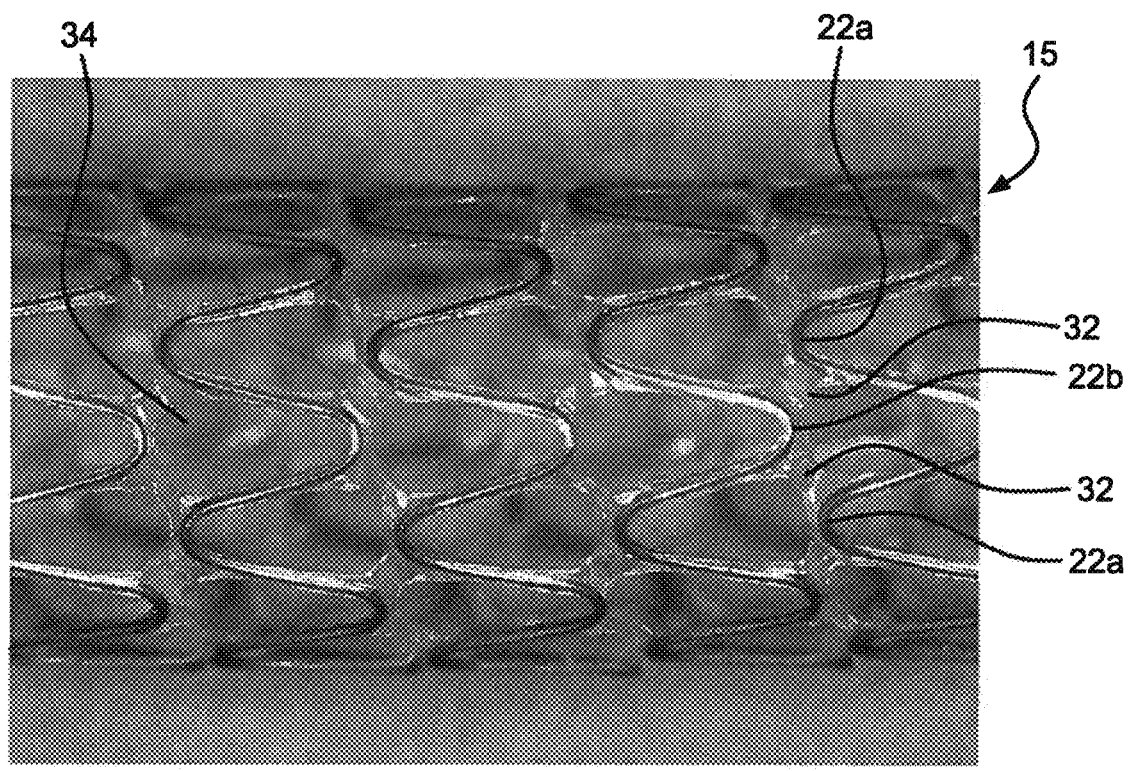
FIG. 2A is a side perspective view of a portion of a helically wound serpentine wire stent provided with flexible interconnecting webs between adjacent stent elements.
Figure 2B:
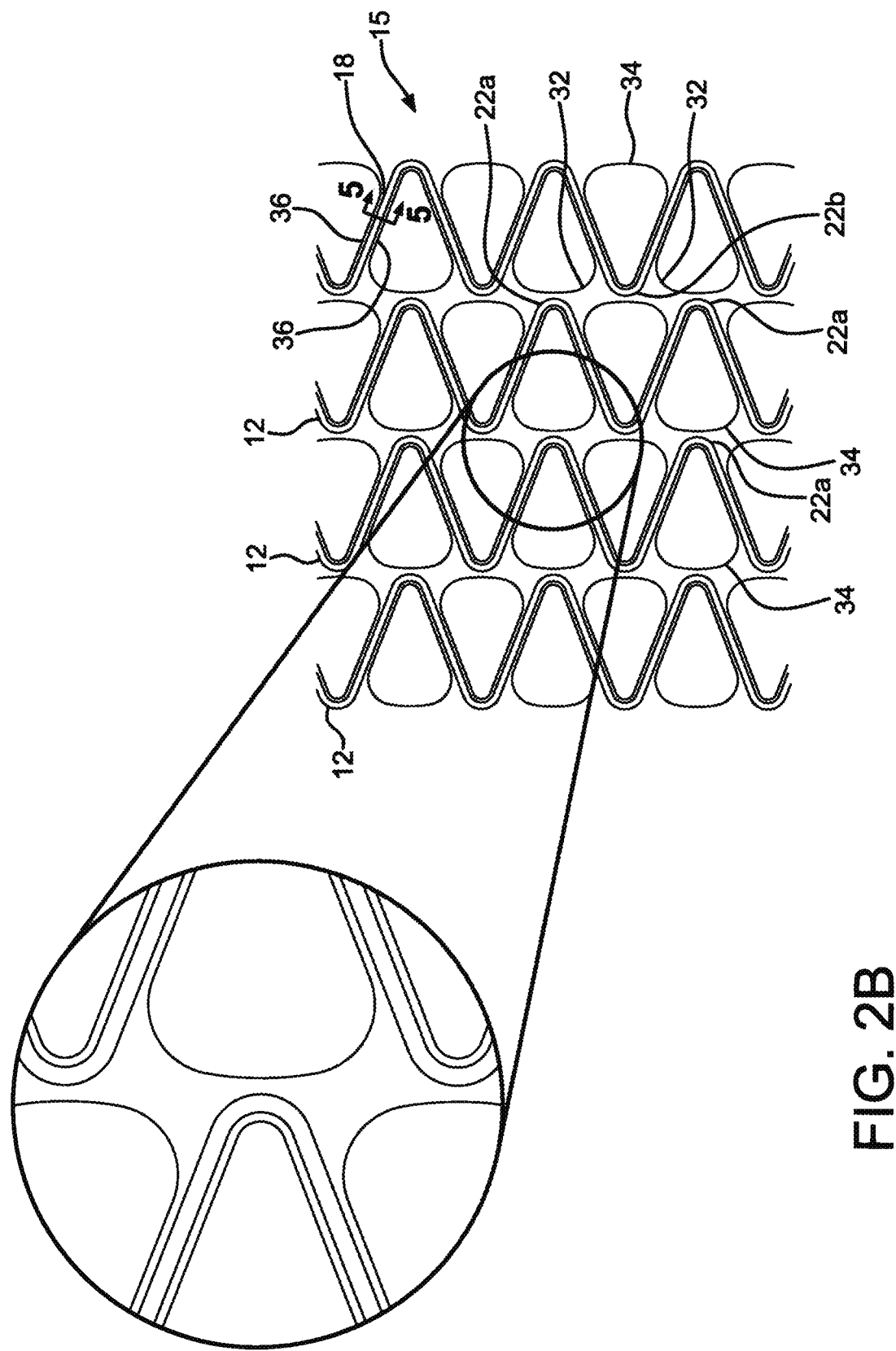
FIG. 2B is a flattened, plan view of the stent of FIG. 2A.

FIG. 2A is a side perspective view of a portion of the length of an open-frame stent 10 wherein spaced-apart, adjacent stent elements 12 (e.g., two adjacent apices 22a connected to opposing apex 22b) are interconnected by a pair of flexible polymeric webs 32. FIG. 2B shows a flattened plan view of this same construction. Openings 34 exist between adjacent aligned apices 22a; the particular single openings 18 are generally in the shape of a guitar pick. If one drew a line through the center of the length of an individual, randomly selected web (i.e., extending between the adjacent wire apices joined by that web), that line would preferably form an angle of between 15 and 75 degrees with respect to a line parallel with the centerline of the stent (or parallel with the centerline 19 of mandrel 16 shown in FIG. 1). Said otherwise, for this type of stent with elements interconnected by flexible webs 32, the webs 32 preferably are oriented at an angle to the length of the stent.

The enlarged portion of FIG. 2B shows how these flexible polymeric webs 32 are narrower at the middle of their length than at the ends where they are attached to the stent element (e.g. the nitinol wire). It also shows how the webs 32 preferably merge tangentially into the stent element where they are joined to and attached to the stent element.

Figure 2C:
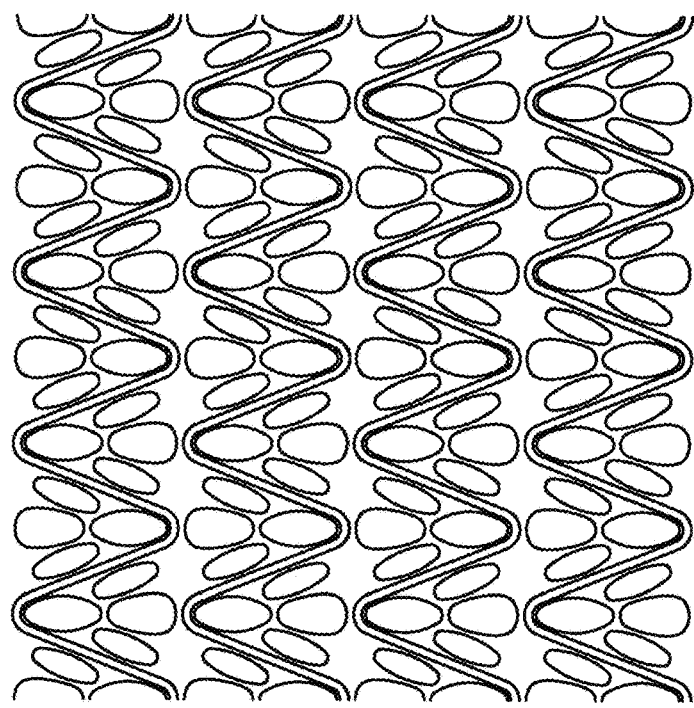
FIGS. 2C and 2D are plan views wherein each single opening shown by FIG. 2B is replaced by multiple apertures, specifically four openings in FIG. 2C and six openings in FIG. 2D.
Figure 2D:
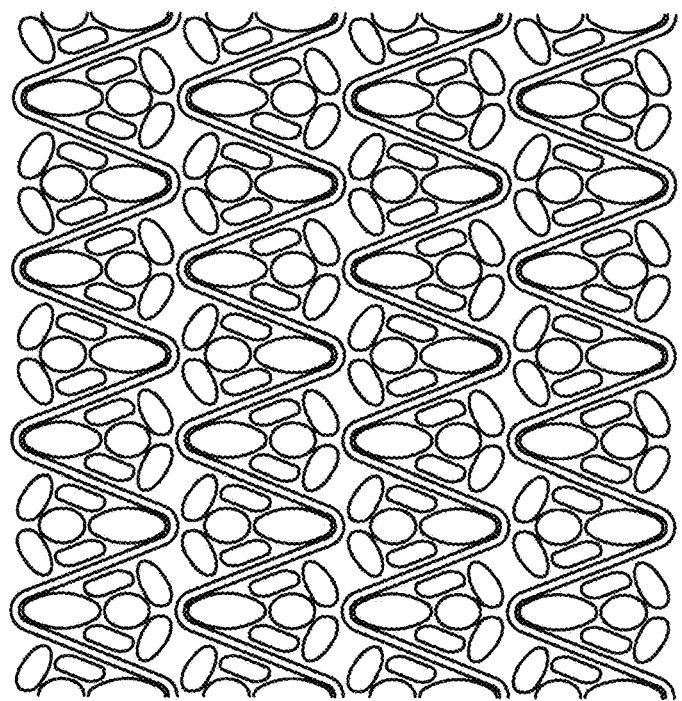

FIGS. 2C and 2D are plan views wherein each single opening shown by FIG. 2B is replaced by multiple apertures, specifically four openings in FIG. 2C and six openings in FIG. 2D.

Figure 3:
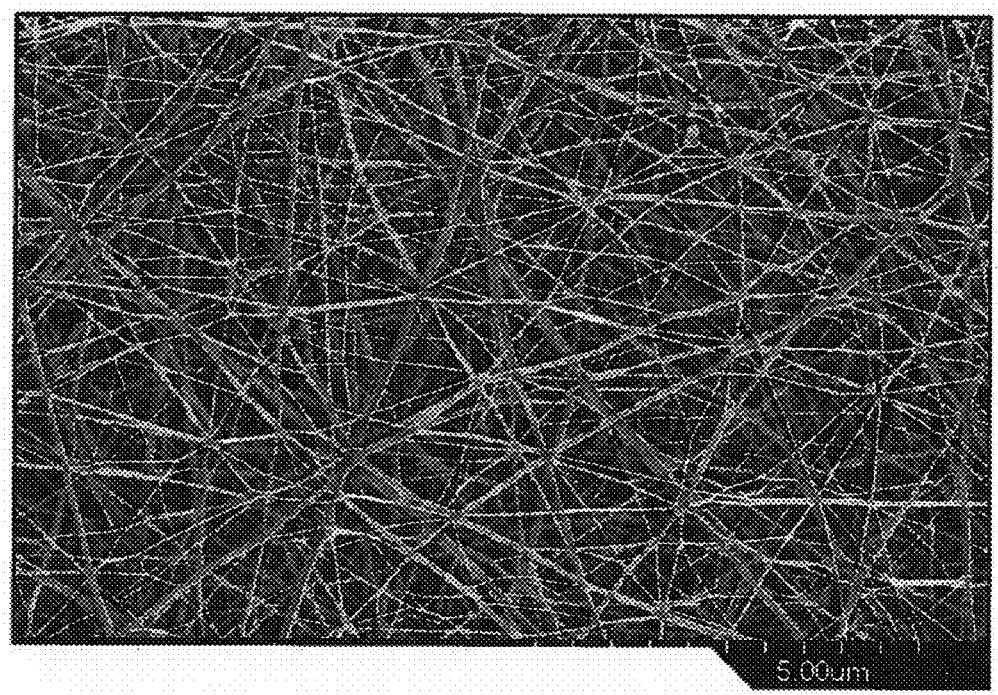
FIG. 3 is a scanning photomicrographs of a multiaxial ePTFE film useful for making the described open frame stent.

While various polymeric films may be suitable for use as the stent covering (or coating) material for this device, combinations of FEP (fluorinated ethylene propylene) films used in combination with ePTFE films are preferred. The preferred ePTFE films for use with these helically wound serpentine wire stents are films having multiaxial fibrillar orientations as shown by the scanning electron photomicrograph of FIG. 3. It is seen how the fibrils are oriented in all directions within the plane of the ePTFE film. ePTFE films of this type may be made as taught by U.S. Pat. No. 7,306,729 and US Published Patent Application 2007/0012624 to Bacino et al. Films of this same type may optionally be provided with a partial covering of a thin layer of FEP (having openings through the FEP film covering; i.e., a discontinuous covering). FEP coated ePTFE films, with either a discontinuous (porous) FEP covering (coating) or a continuous (non-porous) FEP covering (coating) may be made generally as taught by U.S. Pat. No. 5,735,892 to Myers et al.

Figure 4:
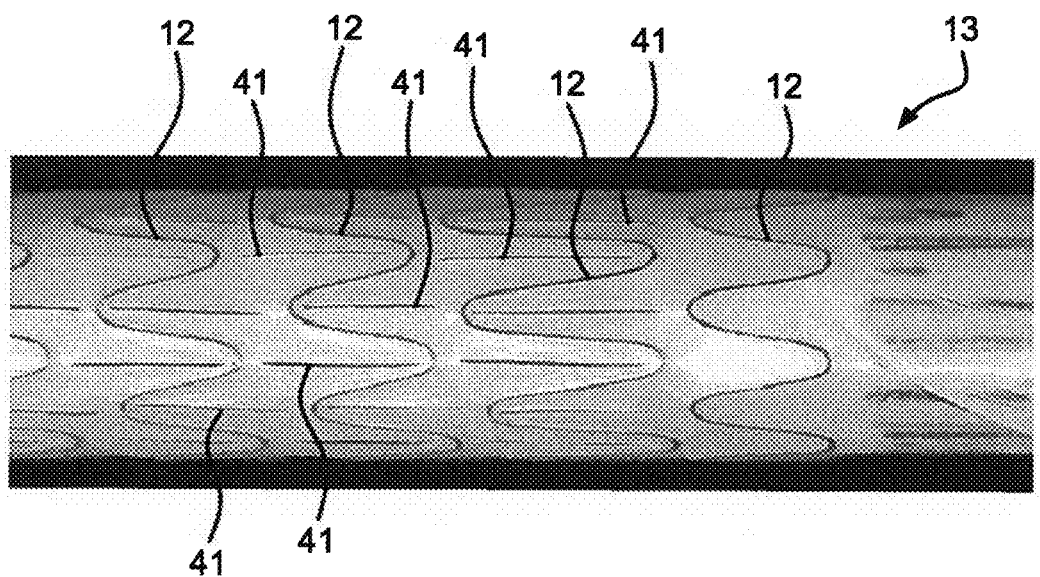
FIG. 4 shows a side view of a partially completed stent provided with slits or punctures that are part of the process of manufacturing the device.

FIG. 4 shows a partially finished stent 13 of helically wound serpentine wire provided with a first outer (abluminal) covering of FEP film and an additional covering of multiaxial ePTFE film, wherein longitudinally oriented slits 41 have been made through the film between adjacent apices of the wire that are pointed in the same direction. Heat will be applied to the device having the multiple slits 41, causing the films to shrink back toward the adjacent wire stent elements, subsequently resulting the openings in the finished stent 15 (FIG. 2A). This process is described in further detail below.

While, as noted, various types of films may be used for the stent covering, the described ePTFE films is preferred because of its multiaxial (within the plane of the film) strength orientation. It is strong, thin, and has excellent biocompatibility. When suitable heat is applied following slitting, the film will retract (shrink back) with good uniformity to create the openings through the polymeric stent covering and to create the flexible polymeric interconnecting webs between adjacent stent elements.

Figure 5A:
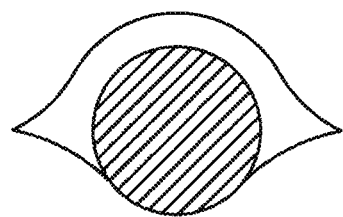
FIGS. 5A-5C show transverse cross sectional views of a stent element as it may appear for a finished stent made as described herein.
Figure 5B:
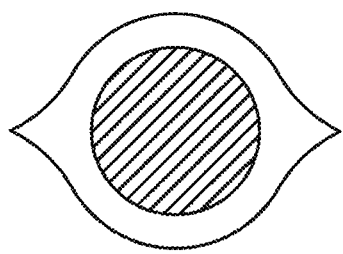
Figure 5C:
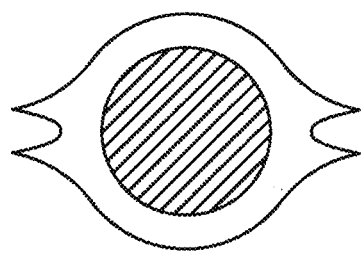

The flexible interconnecting webs 32 that result from this process typically are of wider width at their end points where they connect with the wire apices and are of comparatively narrower width in the middle of their lengths between the apices that they interconnect. Additionally, there may be a very thin, vestigial edge (36, FIG. 2B) of film that extends outwardly away from the wire 18 in the straight portions 24 that connect the apices in the same helical winding (i.e., apices 22a and 22b). FIG. 5A shows a transverse cross section of the wire with this edge (taken at section 5 indicated in the plan view of FIG. 2B) that shows the general appearance of the edge for a single layer of graft material applied to either the outer or inner surface of the stent. FIGS. 5B and 5C show the transverse cross section as it would appear for a covering applied to both the inner and outer surfaces of the stent element.

A preferred method of making a flexible stent is as follows. A stainless steel mandrel of diameter equal to about the inside diameter of the intended stent is obtained. The surface of the mandrel is provided with a helical wrapping of a 1" wide tape of Kapton® Polyimide Film (DuPont, 0.002 inch thickness). A stent of the desired length and diameter made of helically wound serpentine nitinol wire is provided (wire diameter as desired). This is then wound around the Kapton covered surface of the mandrel. The end of the stent wires are secured to an adjacent winding of the stent wire using an FEP thread tied with a securing knot. The apices of the serpentine wire are aligned so that apices pointing in a common direction are aligned with and parallel to the longitudinal axis of the mandrel. The stent is then helically wrapped with a covering of a single layer of FEP tape that has been cut from FEP film (0.00015 inch thickness and about 0.75 inch width), stretched tight over the outer surface of the stent with minimal overlap of adjacent edges of the FEP tape. This FEP tape is then cigarette wrapped (wrapped in a direction perpendicular to the longitudinal axis of the mandrel) with an ePTFE film of the type described previously. This wrapping may be started by aligning a transverse edge of the film with the longitudinal axis of the mandrel and attaching it to the underlying FEP film by carefully melt-bonding the ePTFE film edge to the FEP using a heat source such as a clean soldering iron or appropriate equivalent. Six layers of the ePTFE film are wrapped around the outer surface of the stent and the film edge is trimmed along the length of the stent (i.e., parallel to the longitudinal axis of the mandrel). The film edge is secured with the previously-used heat source.

Longitudinal slits 41 are created between adjacent wire apices that are pointed in the same direction as shown by FIG. 4. These slits may be created by any suitable means, including the use of a scalpel blade, water jet, laser, etc. One such suitable laser is a Coherent Inc., Model: GEM-100A, $CO_2$, CW (continuous wave only), Santa Clara, CA. The last row of apices at each end of the stent may be omitted from slitting if it is desired to leave these end rows covered in their entirety (i.e., in stent-graft fashion). The entire length of the wrapped stent is then provided with an additional, temporary helical wrap of the Kapton tape; the ends of this tape may be secured to the surface of the mandrel beyond each end of the stent with a mechanical clip or other temporary fastener. This layer of Kapton is then tightly wrapped with a temporary helical wrap of ePTFE tape (made from an ePTFE film having a fibrillar microstructure with fibrils oriented predominately parallel to the length of the tape and wrapped with a small pitch angle so that the orientation is primarily circumferential with respect to the mandrel). This ePTFE tape will provide circumferential compression to the underlying materials when suitably heated.

The above construction is them placed into a suitable convection oven set at 380° C. for 11 minutes, after which it is removed from the oven and allowed to cool to approximately ambient temperature. The outer layers of ePTFE film and Kapton tape are then removed. The resulting coated stent and underlying layer of Kapton tape are then carefully removed from the mandrel. The remaining layer of Kapton tape may then be removed from the stent using a suitable tool such as small forceps or tweezers. Remaining film edges protruding beyond the ends of the stent may then be carefully trimmed in a transverse direction close to the end apices of the stent wire with a scalpel blade.

Figure 6A:
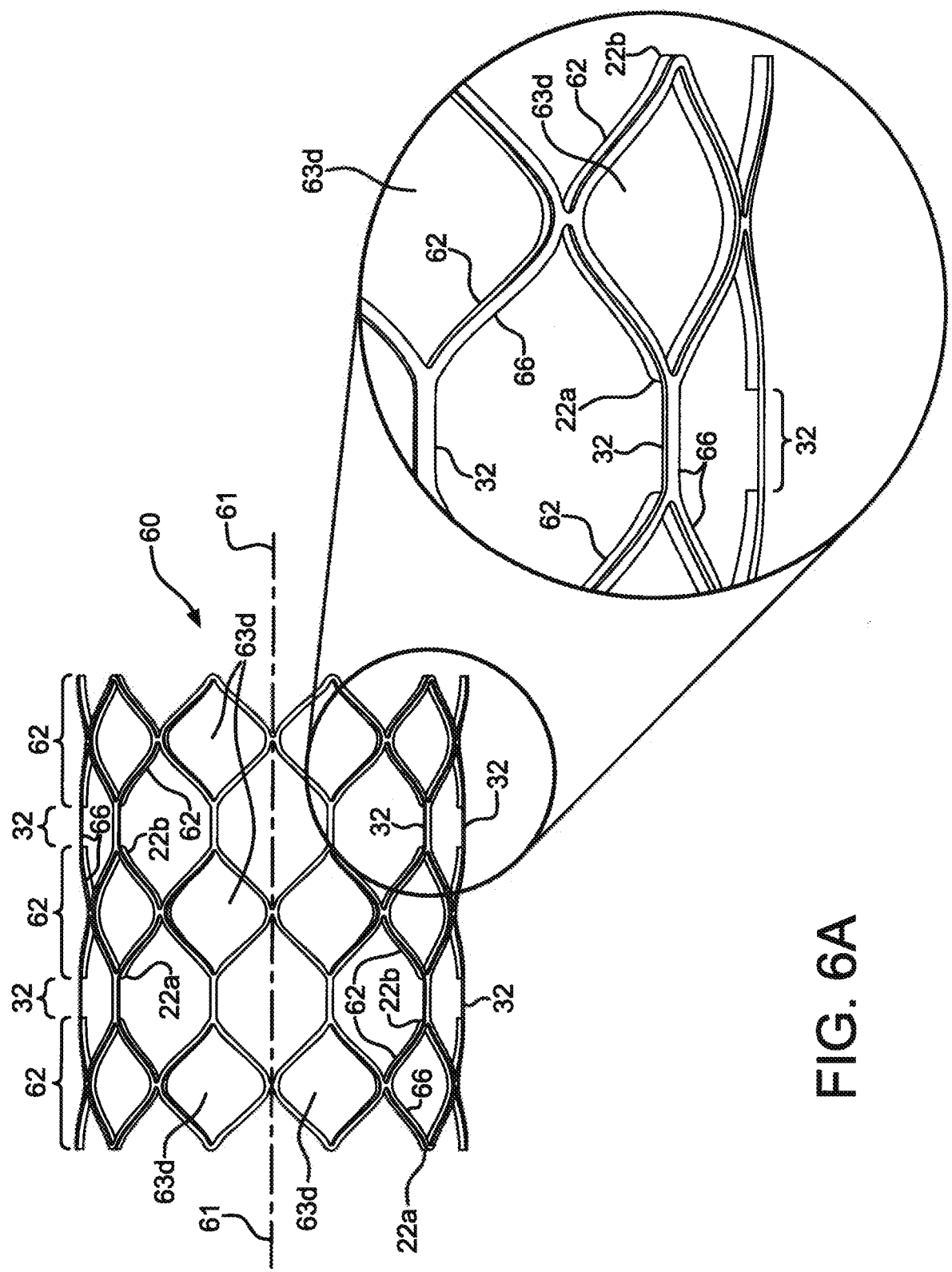
FIG. 6A is a side perspective view of a balloon expandable stent (or a length portion of such a stent) provided with flexible interconnecting webs between adjacent stent elements.

FIG. 6A shows a perspective view of a balloon expandable stent 60, as it appears following diametrical expansion with a balloon that is preferred for use as described herein. The stent 60 shown comprises rings 62 wherein the balloon-expanded stent elements form multiple diamond-shaped openings 63d; stent 60 is typically comprised of one or more of these rings 62. The individual rings 62 may be constructed by any suitable means known in art but are preferably fabricated from a laser cut tube. For clarity, only the side of the tubular stent 60 closest to the viewer is shown. Stent 60 is provided with a polymeric covering 66, preferably of a flexible film. It is apparent how covering 66 interconnects the multiple rings 62 to create stent 60, via webs 32 that span the distance between apices 22a and 22b of adjacent rings 62.

While various polymeric films may be suitable for use as the stent covering (or coating) material for this device, combinations of FEP (fluorinated ethylene propylene) films used in combination with ePTFE films are preferred. The preferred ePTFE film for this device is a uni-axial film having higher strength in one direction, with the direction primarily aligned with the longitudinal axis 61 of the stent prior to balloon expansion. This type of film is similar to that described in U.S. Pat. No. 5,476,589. A further preference would be to modify the film with an application of a discontinuous coating of FEP similar to that taught in U.S. Pat. No. 6,159,565.

Figure 6B:
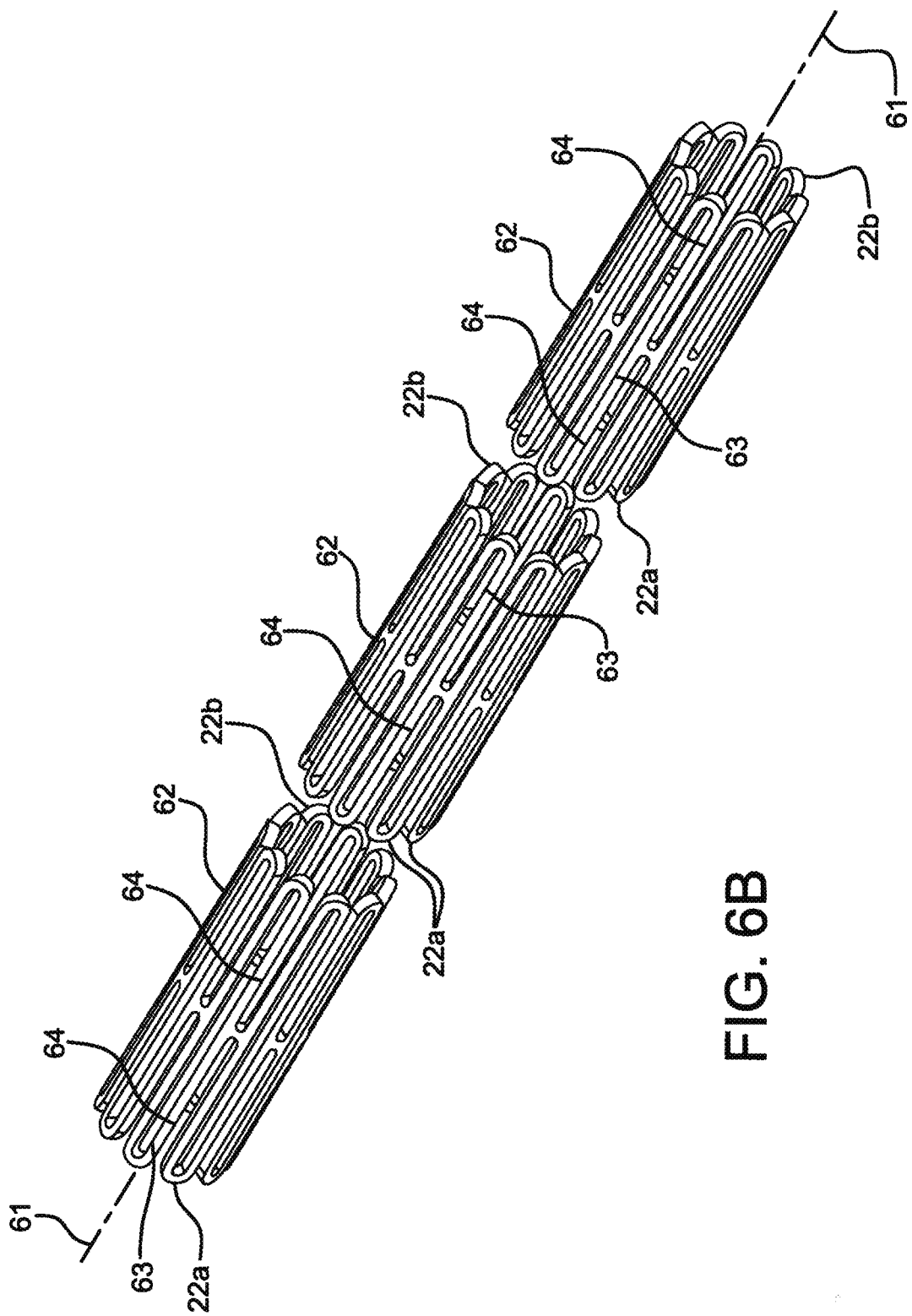
FIG. 6B is a side perspective view of three stent rings shown without the interconnecting polymeric covering.

The arrangement of stent rings 62 are shown in FIG. 6B without polymeric covering 66 as the rings 62 would appear prior to balloon expansion. Unexpanded stent rings 62 are cut to have openings 63 which become diamond shaped openings 63d when expanded (as shown in FIG. 6A). Stent rings 62 are placed in proximity to one another with apices 22a and 22b in a typical apex to apex alignment. It is apparent that the distance between adjacent rings 62 may be as desired.

Figure 6C:
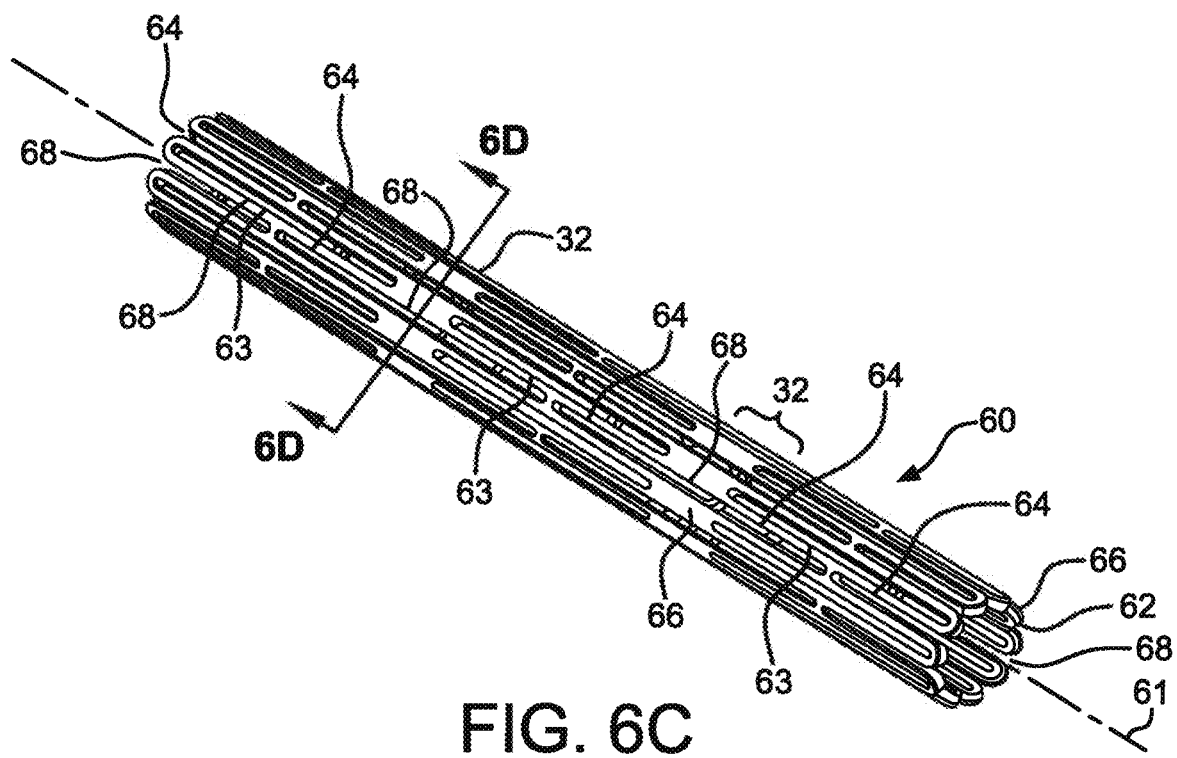
FIG. 6C is a side perspective view of the stent assembly comprising the stent rings shown in 6B provided with the interconnecting polymeric covering.
Figure 6D:
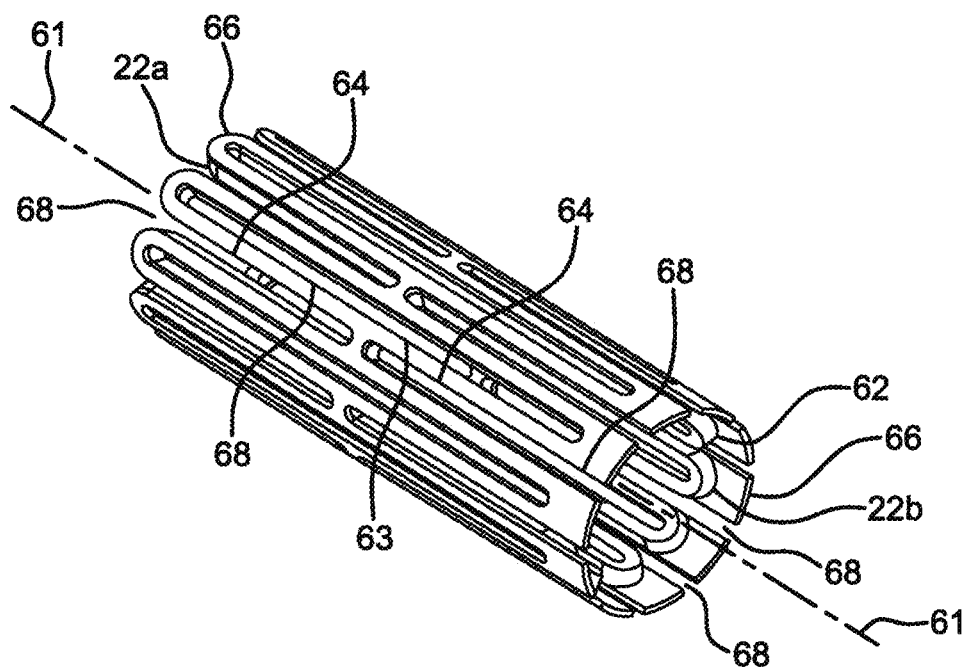
FIG. 6D is the upper left section of the stent assembly described by FIG. 6C, shown as a perspective detail.

FIG. 6C illustrates the stent rings 62 as shown previously in FIG. 6B with the addition of interconnecting polymeric covering 66. Webs 32, each a portion of polymeric covering 66, are shown to interconnect adjacent rings 62. FIG. 6D is an enlarged detail perspective view of the upper left end of stent 60 described in FIG. 6C.

Also shown in FIGS. 6C and 6D are punctures or slits 68 arranged in polymeric covering 66 along the longitudinal axis of stent 60. FIGS. 6B-6D show the multiplicity of openings 63 and 64 formed between adjacent stent elements of stent rings 62. Slits 68 through polymeric covering 66 are formed of size and shape to generally correspond with the multiplicity of openings 63 and 64 in each stent ring 62. These slits 68 may be formed by various means as previously described. Slits 68 are formed through the polymeric covering 66 that covers openings 63 that extend between opposing apices 22a and 22b (openings that are enclosed between the ends of each stent ring 62). Alternate openings 64 that extend from the middle of the length of each stent ring 62 and fully to the end of each stent ring 62 (i.e. between radially adjacent apices 22a and 22a, and likewise between radially adjacent apices 22b and 22b) are also provided with slits through the covering polymeric material 66. These slits 68 extend longitudinally between adjacent rings 62 and into the corresponding opening in the adjacent ring 62. These slits 68 collectively create individual interconnecting webs 32. Slits 68 may be of width as desired; the width of a scalpel blade may be deemed sufficient even though the figures show that width of slit 68 corresponding to the width of the underlying stent openings 63 and 64.

Figure 7:
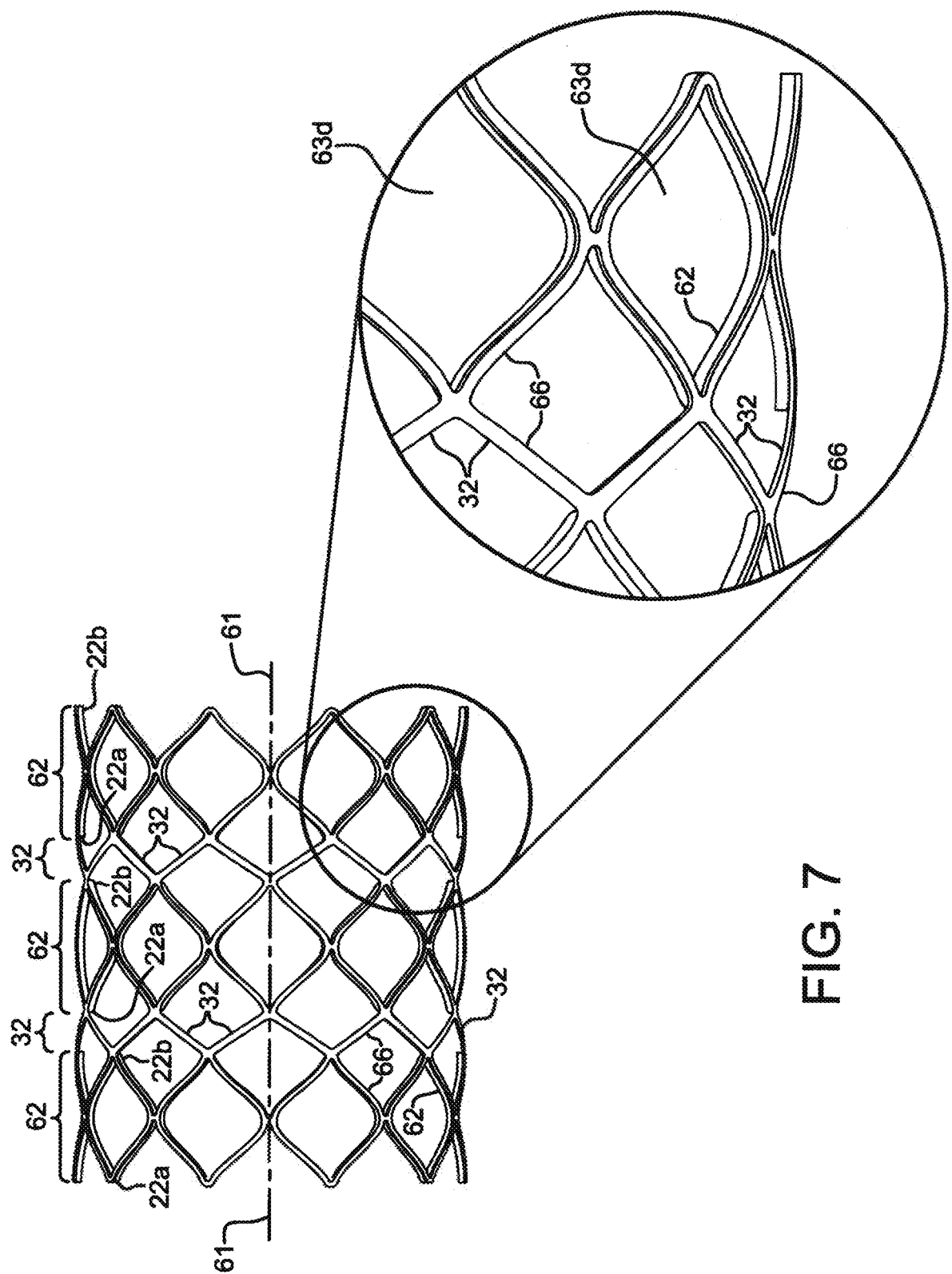
FIG. 7 is a side perspective view of a balloon expandable stent (or a length portion of such a stent) provided with flexible interconnecting webs between adjacent stent elements.

The apices 22a and 22b of each ring 62 may be made to point toward one another as shown in FIG. 6A or may be arranged to be offset as shown in FIG. 7 (i.e. aligned peak-to-valley as shown in FIG. 7 as opposed to being aligned in peak-to-peak fashion as shown in FIGS. 1A through 2D, FIG. 4 and FIG. 6A). The apices typically "point" in directions that are substantially parallel to the longitudinal axis 61 of the tubular form of the stent 60.

Figure 8:
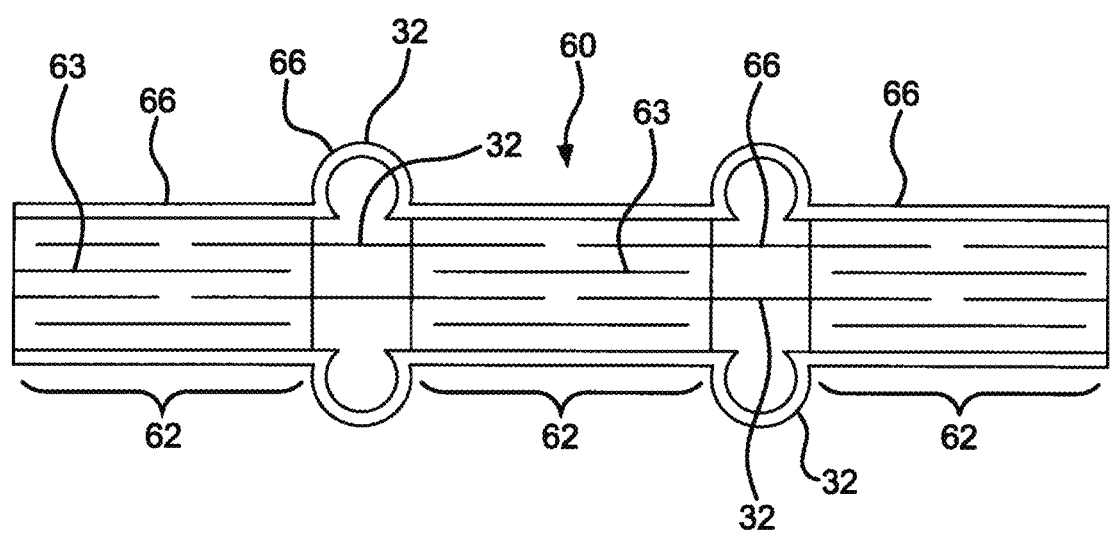
FIG. 8 is a schematic side view of stent as it would appear when mounted on a balloon for subsequent deployment and expansion.

FIG. 8 is a schematic side view of stent 60 as it would appear mounted on a balloon (not shown) for subsequent deployment and expansion. Stent 60 is preferably axially compressed during mounting so that Interconnecting webs 32 are bowed or wrinkled so that stent 60 is foreshortened. The advantage of mounting stent 60 in this fashion is that, during balloon expansion, stent rings 62 will foreshorten as they are deformed (with openings 63 becoming diamond shaped openings 63d). For example, this allows for less than 10% shortening with a greater than 6 times diametrical expansion. Bowed webs 32 may be tucked under adjacent stent ring 62 if it is preferred that they do not protrude outwardly. A preferred balloon is a balloon that expands diametrically from the middle of its length toward its opposing ends. Alternatively, stent rings 62 at the ends of stent 60 may be made of a thicker material than ring 62 positioned closer to the middle of the length of stent 60. These alternatives result in the application of tension during expansion to bowed webs 32 thereby pulling the slack out of them, increasing their length and compensating for foreshortening of rings 62 to maintain the length of stent 60.

A preferred method of making a stent such as a stent shown in FIGS. 6A through 7 is as follows. Standard diamond pattern geometry stents were laser machined and electro-polished at Laserage Technology Inc, Waukegan, IL from a 316 LVM stainless steel tube measuring 4.19 mm diameter×0.38 mm wall thickness, available from Norman Noble, Cleveland OH. The stents were exposed to a surface roughening step to improve adherence without degrading fatigue durability performance. Plasma treatment of the stents was performed prior to FEP powder coating for purposes of cleaning and reducing contact angle of the metal surface. Plasma treatment was performed as commonly known in the arts.

FEP powder (Daikin America, Orangeburg N.Y.) was applied to the stent component by first stirring the powder into an airborne "cloud" in a standard kitchen-type blender and suspending the frame in the cloud until a uniform layer of powder was attached to the stent frame. The stent component was then subjected to a thermal treatment of 320° C. for approximately three minutes. This caused the powder to melt and adhere as a coating over the stent component. Each ring was coated a second time while suspending it from the opposite end and placed in 320° C. oven for 3 minutes then removed and allowed to cool to room temperature.

Seventeen layers of a thin ePTFE film provided with a discontinuous coating of FEP as previously described was then wrapped around a stainless steel mandrel measuring approx 3.43 mm. The film is applied with its high strength orientation parallel to the longitudinal axis of the stent and with the FEP side facing out. Individual stent rings were placed over the film tube and aligned. In this case, the stent rings were aligned apex to apex and separated evenly with a gap of about 2.5 mm between each ring to achieve an overall device length of about 40 mm. An additional 17 layers of the same film was applied as previously described except with the FEP side oriented down, toward the outer diameter of the stent.

The entire assembly was wound with several layers of an ePTFE thread (Part #SO24T4, WL Gore, Elkton, MD) to impart compressive forces to the underlying construct. The assembly was placed in 320° c. oven (Grieves, Model MT1000, The Grieve Corporation, Round Lake, IL) for approximately 40 minutes. The stent assembly was removed and allowed to cool to room temperature. The over-wrap was then removed and the slits were created and excess material was removed.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. An endoprosthesis having a length, a radius, and a circumference, the endoprosthesis comprising:
    a stent having a plurality of stent elements forming a serpentine pattern with multiple apices; and
    at least two polymeric webs that attach a first apex of a first stent element of the plurality of stent elements to at least two positions of a second stent element of the plurality of stent elements.

2. The stent according to claim 1, wherein the plurality of stent elements are in the form of helically wound wire.

3. The stent according to claim 2, wherein said wire comprises nitinol.

4. The stent according to claim 1, wherein said polymeric webs comprise ePTFE.

5. The stent according to claim 4, wherein said polymeric webs further comprise fluorinated ethylene propylene.

6. The stent according to claim 1, wherein said stent elements comprise stainless steel.

7. The stent according to claim 1, wherein said stent is an open frame stent.

8. The stent according to claim 1, wherein said polymeric webs are melt-bonded to said stent elements.

9. The stent according to claim 1, wherein said stent has a length and said polymeric webs are continuous along said length.

10. The stent according to claim 1, wherein the at least two polymeric webs define a first opening positioned between the first stent element and the second stent element, the first opening having a first shape; and a second opening positioned between the first stent element and the second stent element, the second opening having a second shape different than the first shape.

11. An endoprosthesis having a length, a radius, and a circumference, the endoprosthesis comprising:
a stent having a plurality of windings with multiple apices; and
a polymeric web attaching an apex of a first winding of the plurality of windings with a second winding of the plurality of windings, wherein a center of a length of the polymeric web forms an angle of between 15 and 75 degrees with respect to a line parallel with a longitudinal centerline of the stent.

12. The endoprosthesis of claim 11, wherein the polymeric web is formed of a film.

13. The endoprosthesis of claim 11, wherein the polymeric web has a first width at a middle portion of said polymeric web and a second width at an end portion of said polymeric web adjacent to either of the first winding or the second winding, the first width being less than the second width.

14. The endoprosthesis of claim 11, wherein the polymeric web merges tangentially into at least one of the first winding or the second winding.

15. The endoprosthesis of claim 11, further comprising a second polymeric web attaching the apex of the first winding to a second position on the second winding.

16. The endoprosthesis of claim 15, wherein the second position on the second winding is a straight portion between two apices of the second winding.

17. An endoprosthesis having a length, a radius, and a circumference, the endoprosthesis comprising:
a stent having a plurality of stent elements forming a plurality of apices, each apex connected to an adjacent apex with a straight portion of the stent element; and
a film web extending from an apex of a first stent element of the plurality of stent elements to a second stent element of the plurality of stent elements, the film web including an extension which extends along a straight portion of the first stent element so that the first stent element is covered by the film web.

18. The endoprosthesis of claim 17, wherein the film web further includes a second extension which extends away from the straight portion of the first stent element toward the second stent element of the plurality of stent elements.

19. The endoprosthesis of claim 17, wherein the film web covers an entire length of the first stent element between adjacent apices.

20. The endoprosthesis of claim 17, wherein the film web defines openings in the endoprosthesis.

* * * * *